(12) United States Patent
Okawa et al.

(10) Patent No.: US 8,521,261 B2
(45) Date of Patent: *Aug. 27, 2013

(54) LESION EXTRACTING DEVICE AND LESION EXTRACTING METHOD

(75) Inventors: Atsushi Okawa, Tokyo (JP); Tianyu Xie, Tokyo (JP); Toshiaki Watanabe, Tokyo (JP); Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/359,671

(22) Filed: Jan. 27, 2012

(65) Prior Publication Data

US 2012/0197134 A1 Aug. 2, 2012

Related U.S. Application Data

(63) Continuation of application No. 11/805,228, filed on May 22, 2007, now Pat. No. 8,131,349.

(30) Foreign Application Priority Data

May 29, 2006 (JP) ................................. 2006-148038

(51) Int. Cl.
    *A61B 5/05* (2006.01)
(52) U.S. Cl.
    USPC .......................................... 600/477; 600/478

(58) Field of Classification Search
    USPC .................................................. 600/477–478
    See application file for complete search history.

(56) References Cited

U.S. PATENT DOCUMENTS

| 5,749,830 A * | 5/1998 | Kaneko et al. ................ 600/160 |
| 2003/0004418 A1 * | 1/2003 | Marmorstein ................ 600/475 |

FOREIGN PATENT DOCUMENTS

| JP | Hei 07-222712 A | 8/1995 |
| JP | 2004-000477 A | 1/2004 |

* cited by examiner

*Primary Examiner* — Jonathan Cwern
(74) *Attorney, Agent, or Firm* — Scully, Scott, Murphy & Presser, P.C.

(57) ABSTRACT

A lesion extracting device includes a light source for emitting an excitation light toward a subject body, a control unit for changing an amount of the excitation light, a light irradiating and receiving portion for irradiating the excitation light to the subject body and receiving fluorescence generated from the subject body, a distance holding member for holding a distance between the subject body and the light irradiating and receiving portion at a predetermined value, a measuring unit for measuring the intensity of the fluorescence received by the light irradiating and receiving portion, and an extracting unit for extracting a lesion part of the subject body based on relationships between measured values of changes in the fluorescence intensity with respect to changes in the amount of the excitation light and information regarding the changes in the amount of the excitation light, the information being obtained from the control unit.

3 Claims, 12 Drawing Sheets

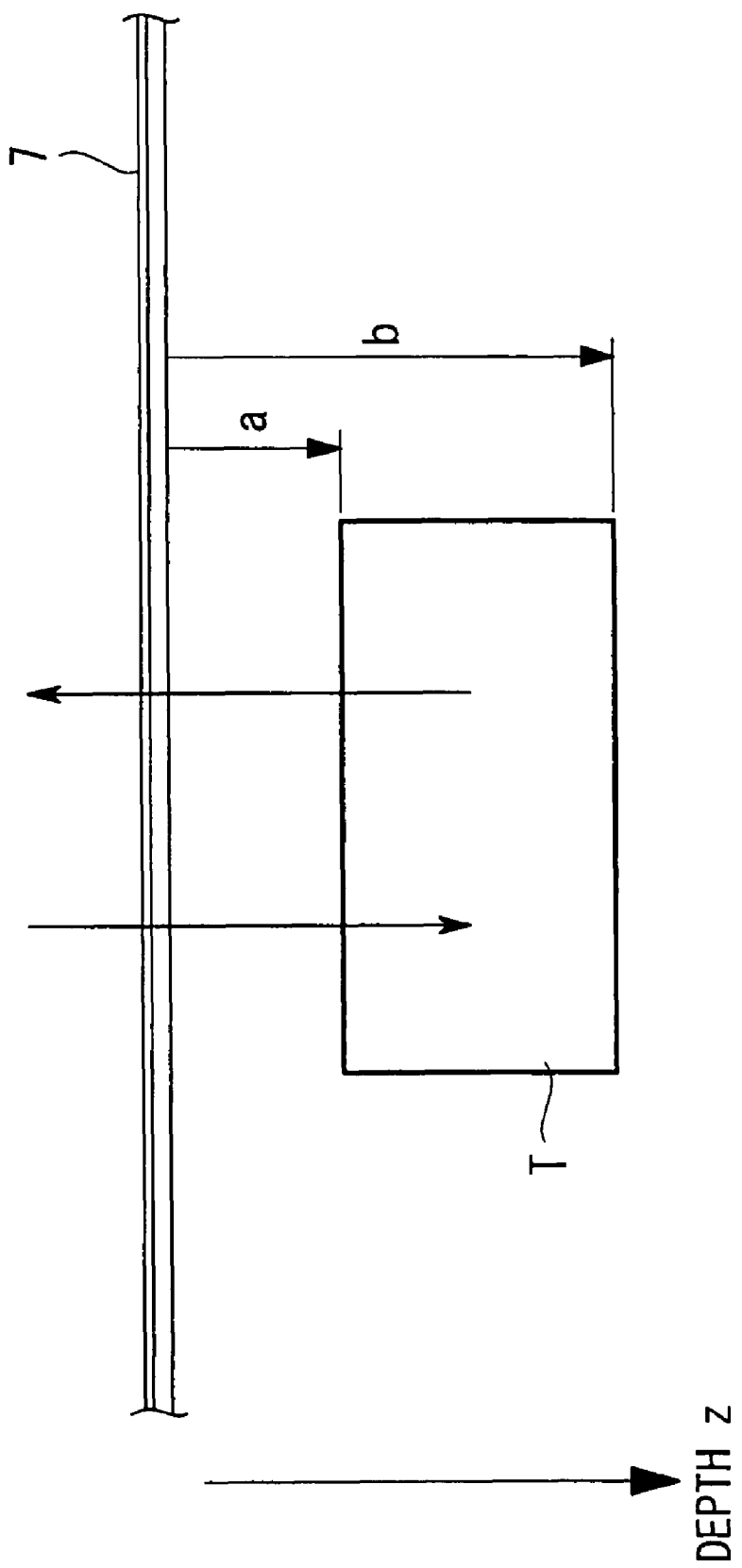

LESION EXTRACTING DEVICE AND LESION EXTRACTING METHOD

CROSS-REFERENCE TO RELATED APPLICATIONS

This application is a continuation of application Ser. No. 11/805,228, filed on May 22, 2007, which claims the benefit of Japanese Patent Application No. 2006-148038, the content of which is incorporated herein by reference.

BACKGROUND OF THE INVENTION

1. Field of the Invention

The present invention relates to a lesion extracting device and a lesion extracting method, which can determine a lesion part based on a fluorescence image produced with irradiation of an excitation light.

2. Description of Related Art

Recently, development has been progressed on a technique for diagnosing a cancer or other affected state of body tissues by using a medicament which is accumulated in an affected part, such as a cancer, and which emits fluorescence with irradiation of an excitation light.

In particular, there is known a technique of irradiating an excitation light to a biomedical body from, e.g., a fluorescence endoscope after injection of the medicament into the body, detecting fluorescence generated from the medicament, which has been accumulated in the affected part, in the form of a two-dimensional image by using, e.g., the fluorescence endoscope, and diagnosing the affected part based on the detected fluorescence image (see, for example, Japanese Unexamined Patent Application, Publication No. Hei 7-222712 and No. 2004-477).

The above-described diagnosis using fluorescence has the problem as follows. When a normal part and a lesion part or a benign tumor and a malignant tumor are present in the same field of view for observation, it is often difficult to discriminate the normal part and the lesion part or the benign tumor and the malignant tumor from each other.

More specifically, in the diagnosis using fluorescence, comparing the normal part and the lesion part, the intensity of fluorescence generated from the lesion part is stronger than that emitted from the normal part. Comparing the benign tumor and the malignant tumor, the intensity of fluorescence generated from the malignant part is stronger than that generated from the benign part. In general, the intensity of the fluorescence generated from the lesion part is proportional to the intensity of the excitation light irradiated to the lesion part. Accordingly, when the intensity of the excitation light irradiated to the normal part (benign tumor) is stronger than the intensity of the excitation light irradiated to the lesion part (malignant tumor), the intensity of the fluorescence generated from the normal part or the like is stronger than that generated from the lesion part or the like. The above-mentioned problem may occur, for example, when the distance from the tip of an insertion probe of the fluorescence endoscope differs between the normal part and the lesion part or between the benign tumor and the malignant tumor.

Another problem is that, even when the distances to the normal part and the lesion part are substantially the same, a difficulty may occur in discriminating the normal part and the lesion part or the benign tumor and the malignant tumor in some cases.

More specifically, when the lesion part or the like is positioned inside the body, the intensity of the fluorescence generated from the lesion part or the like is attenuated while passing through the body. In such a case, when simultaneously observing the fluorescence generated from the lesion part or the like and the fluorescence generated from the normal part or the like which is positioned at the body surface, the difference between the intensity of the fluorescence generated from the normal part or the like and the intensity of the fluorescence generated from the lesion part or the like is reduced. In other words, the intensity of the fluorescence generated from the lesion part or the like is reduced. This may cause a difficulty in discriminating the normal part and the lesion part or the benign tumor and the malignant tumor from each other.

As one of other methods for quantitatively discriminating the normal part the lesion part, there is known a method comprising the steps of irradiating an excitation light having a plurality of wavelengths to a part to be observed, and analyzing a fluorescence spectrum emitted from the observed part. However, because the fluorescence spectrum contains a very large amount of information, the above method has the problem that it is difficult to extract predetermined information, which is used for determining the normal part and the lesion part, from the fluorescence spectrum and to perform a quantitative analysis.

BRIEF SUMMARY OF THE INVENTION

According to a first aspect, the present invention provides a lesion extracting device comprising a light source for emitting an excitation light toward a subject body to be examined, a control unit for changing an amount of the excitation light, a light irradiating and receiving portion for irradiating the excitation light to the subject body and receiving fluorescence generated from the subject body, a distance holding member for holding a distance between the subject body and the light irradiating and receiving portion at a predetermined value, a measuring unit for measuring the intensity of the fluorescence received by the light irradiating and receiving portion, and an extracting unit for extracting a lesion part of the subject body based on relationships between measured values of changes in the fluorescence intensity with respect to changes in the amount of the excitation light and information regarding the changes in the amount of the excitation light, the information being obtained from the control unit.

In the first aspect of the present invention, preferably, the extracting unit extracts the lesion part based on a ratio of the changes in the amount of the excitation light to the changes in the fluorescence intensity.

In the first aspect of the present invention, preferably, the lesion extracting device further comprises an image producing unit for producing an image based on an output of the extracting unit, and a display unit for displaying the image produced by the image producing unit.

In the above arrangement, preferably, the display unit displays the image when the amount of the excitation light is constant, and does not display the image when the amount of the excitation light is changed.

In the first aspect of the present invention, preferably, the control unit executes control to repeat a constant period in which the amount of the excitation light is kept constant and a change period in which the amount of the excitation light is changed.

In the first aspect of the present invention, preferably, the control unit executes control to keep the amount of the excitation light constant and to change the amount of the excitation light at predetermined timing.

In the above arrangement, preferably, the control unit executes control to continuously change the amount of the excitation light, the image producing unit produces the image at predetermined timing, and the display unit displays the image.

According to a second aspect, the present invention provides a lesion extracting device comprising a light source for emitting an excitation light toward a subject body to be examined, a control unit for executing control to change a wavelength and an amount of the excitation light, a measuring unit for measuring the intensity of fluorescence generated from the subject body, and an extracting unit for extracting a lesion part of the subject body based on relationships between measured values of changes in the fluorescence intensity with respect to changes in the amount of the excitation light and information regarding the changes in the amount of the excitation light, the information being obtained from the control unit.

In the second aspect of the present invention, preferably, the lesion extracting device further comprises a light irradiating and receiving portion for irradiating the excitation light to the subject body and receiving the fluorescence generated from the subject body, and a distance holding member for holding a distance between the subject body and the light irradiating and receiving portion at a predetermined value.

In the first and second aspects of the present invention, preferably, the lesion extracting device further comprises an excitation light filter allowing only the excitation light emitted from the light source to pass therethrough toward the subject body, and a fluorescence filter allowing only the fluorescence emitted from the subject body to pass therethrough toward the measuring unit.

According to a third aspect, the present invention provides a lesion extracting method comprising a light amount changing step of changing an amount of an excitation light emitted toward a subject body to be examined, a distance holding step of holding a distance between the subject body and a light irradiating and receiving portion, which irradiates the excitation light to the subject body and receives fluorescence generated from the subject body, at a predetermined value, a light irradiating and receiving step of irradiating the excitation light to the subject body and receiving the fluorescence generated from the subject body through the light irradiating and receiving portion, a fluorescence intensity measuring step of measuring the intensity of the received fluorescence, and an extracting step of extracting a lesion part of the subject body based on relationships between measured values of changes in the fluorescence intensity with respect to changes in the amount of the excitation light and the changes in the amount of the excitation light, the changes in the amount of the excitation light being performed in the light amount changing step.

In the third aspect of the present invention, preferably, the fluorescence intensity measuring step measures a maximum value and a minimum value of the fluorescence intensity, and the extracting step extracts the lesion part of the subject body based on relationships between the maximum value and the minimum value of the fluorescence intensity with respect to the changes in the amount of the excitation light and a maximum value and a minimum value of the amount of the excitation light.

In the third aspect of the present invention, preferably, the lesion extracting method further comprises, prior to the fluorescence intensity measuring step, a detecting step of detecting a high fluorescence intensity area in which the fluorescence generated from the subject body has high intensity, wherein the fluorescence intensity measuring step measures a maximum value and a minimum value of the fluorescence intensity in the high fluorescence intensity area.

According to a fourth aspect, the present invention provides a lesion extracting method comprising a calculation preparatory step of changing a wavelength and an amount of an excitation light emitted toward a subject body to be examined, irradiating the excitation light to the subject body and receiving fluorescence generated from the subject body, measuring the intensity of the received fluorescence, and deriving relational expressions between a plurality of amounts of the excitation light and a plurality of fluorescence intensities, a calculating step of calculating a thickness of a fluorescence generating area based on the relational expressions between the amounts of the excitation light and the fluorescence intensities, and a determining step of determining, based on the calculated thickness of the fluorescence generating area, whether the fluorescence generating area is a lesion part.

In the fourth aspect of the present invention, preferably, the calculation preparatory step includes a first measuring step of irradiating an excitation light of one wavelength in one amount to the subject body, and measuring the intensity of one kind of fluorescence emitted from the subject body with irradiation of the excitation light of one wavelength, a second measuring step of irradiating an excitation light of another wavelength in the one amount to the subject body, and measuring the intensity of another kind of fluorescence emitted from the subject body with irradiation of the excitation light of the other wavelength, a third measuring step of irradiating the excitation light of the other wavelength in another amount to the subject body, and measuring the intensity of the other kind of fluorescence emitted from the subject body with irradiation of the excitation light of the other wavelength, and a relational expression step of deriving a relational expression between the amount of the excitation light and the fluorescence intensity in the first measuring step, a relational expression between the amount of the excitation light and the fluorescence intensity in the second measuring step, and a relational expression between the amount of the excitation light and the fluorescence intensity in the third measuring step, wherein the other amount of the excitation light in the third measuring step is set such that the intensity of the one kind of fluorescence in the first measuring step and the intensity of the other kind of fluorescence in the third measuring step are substantially equal to each other.

BRIEF DESCRIPTION OF THE SEVERAL VIEWS OF THE DRAWINGS

FIG. 12 a schematic view of a subject body to be examined, the view for explaining parameters of equations derived in an extracting unit.

DETAILED DESCRIPTION OF THE INVENTION

[First Embodiment]

An endoscope device according to a first embodiment of the present invention will be described below with reference to FIGS. 1-6.

Figure 1:
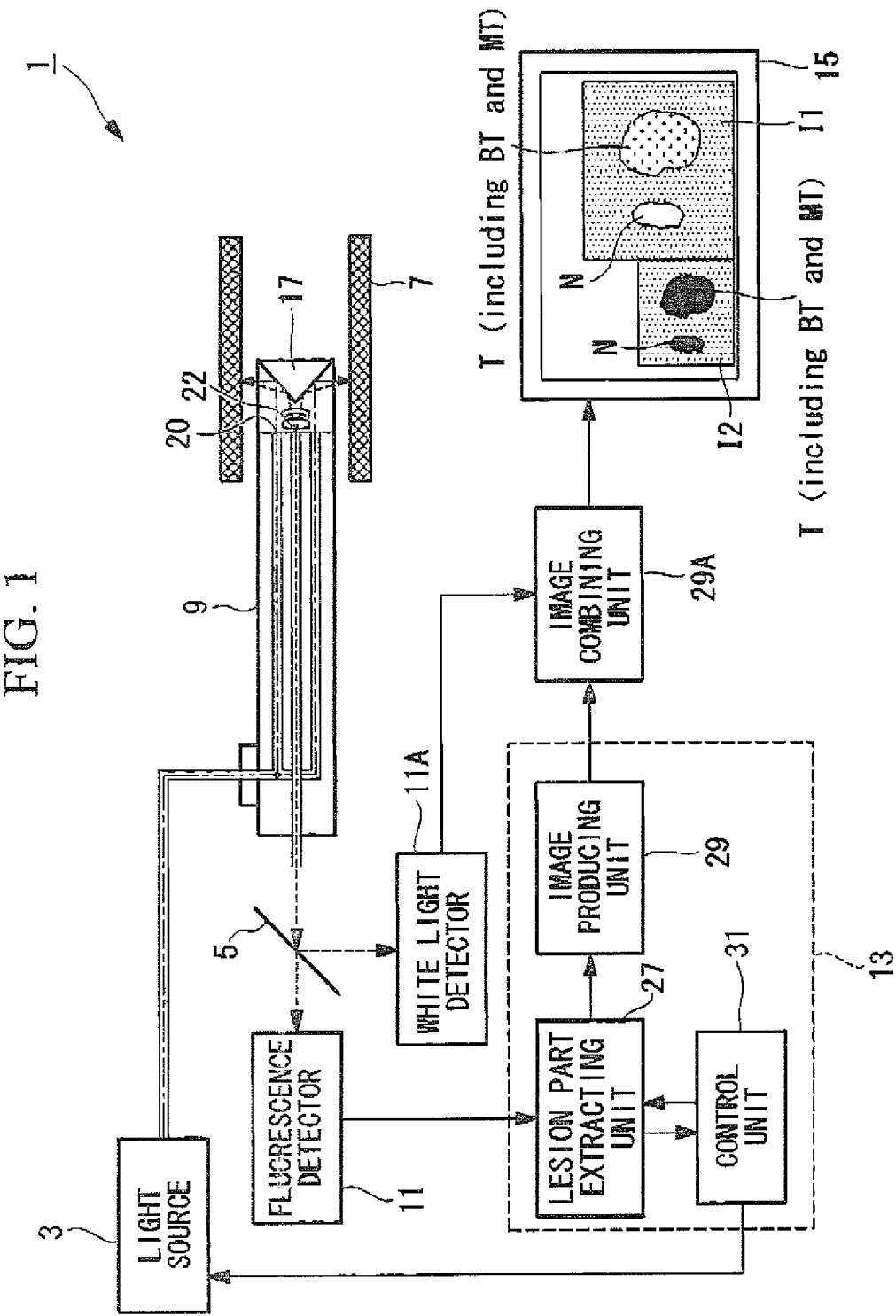
FIG. 1 is a block diagram for explaining a general construction of an endoscope device according to a first embodiment of the present invention.

FIG. 1 is a block diagram for explaining a general construction of the endoscope device according to this first embodiment.

An endoscope device (lesion extracting device) 1 comprises, as shown in FIG. 1, a light source 3 for emitting an excitation light, a half mirror 5 allowing fluorescence to pass therethrough and reflecting a white light, an insertion probe 9 which is inserted into a subject body 7 to be examined, a fluorescence detector (measuring unit) 11 for measuring fluorescence, a white light detector 11A for detecting a white light, a computer (hereinafter abbreviated as a "PC") 13 for performing, e.g., extraction of a lesion part T, an image combining unit 29A for combining an image formed by the white light with an image of the extracted lesion part T, and a monitor (display unit) 15 for displaying the combined image.

The light source 3 emits the excitation light irradiated to the subject body 7. A control signal from a control unit 31 in the PC 13 is input to the light source 3, and the light source 3 changes the amount of the excitation light in accordance with the control signal.

The half mirror 5 allows fluorescence generated from the subject body 7 to pass therethrough, while it reflects a white light, which has been reflected by the subject body 7, toward the white light detector 11A. The half mirror 5 is disposed between the insertion probe 9 and the fluorescence detector 11 in a posture inclined so as to reflect the white light outgoing from the inserted probe 9 toward the white light detector 11A.

Figure 2:
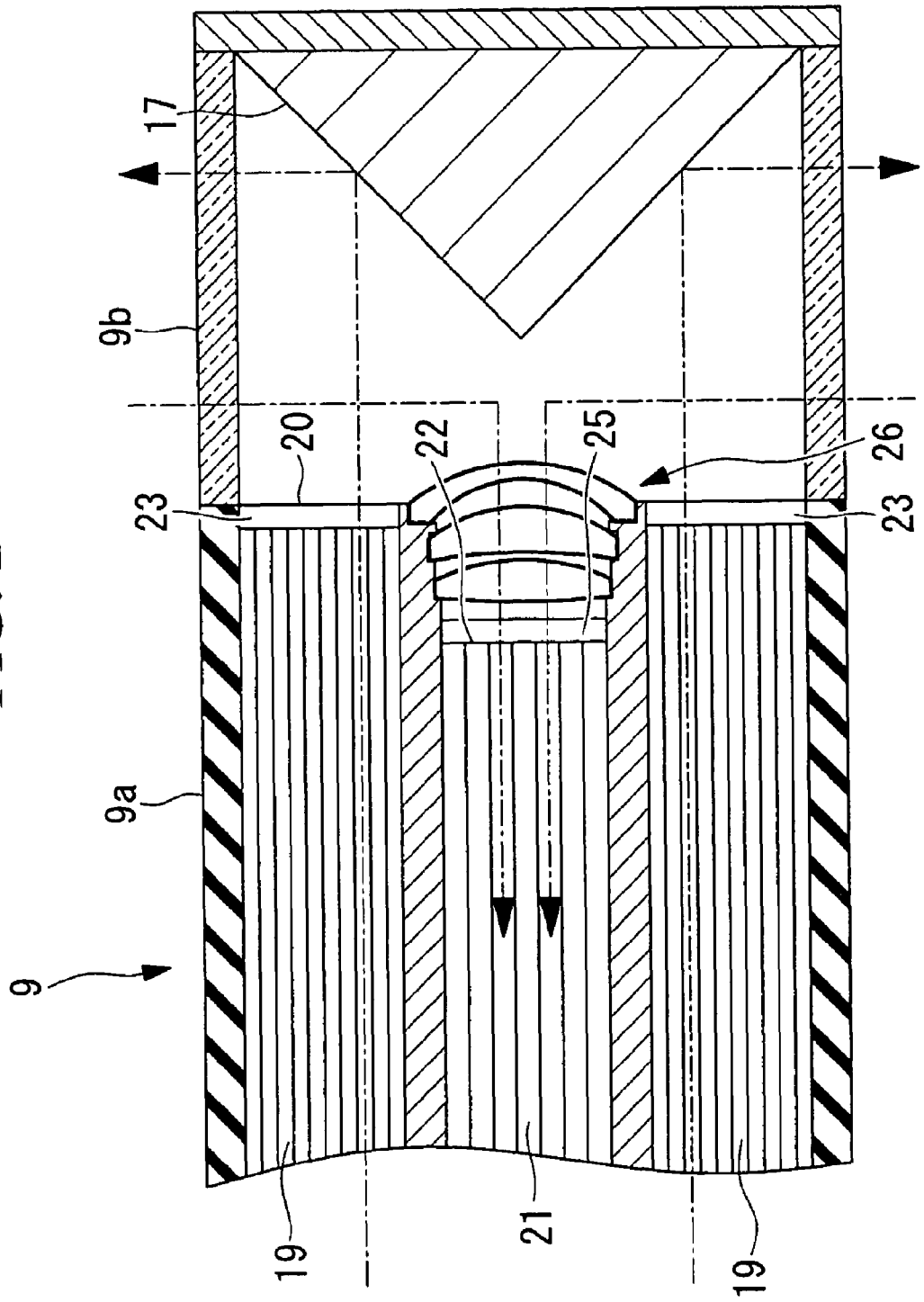
FIG. 2 is a schematic view for explaining one structure of an inserted-side end portion of the endoscope device shown in FIG. 1.

FIG. 2 is a schematic view for explaining the structure of an inserted-side end portion of the endoscope device shown in FIG. 1.

The insertion probe 9 serves not only to introduce the excitation light from the light source 3 into the subject body 7, but also to introduce the fluorescence and the white light from the subject body 7 to the fluorescence detector 11 and the white light detector 11A, respectively. As shown in FIG. 2, the insertion probe 9 comprises a cone mirror (distance holding member) 17 arranged at the inserted-side end (hereinafter referred to as the "distal end") of the insertion probe 9, a light guide 19 for guiding the excitation light, an image guide 21 for guiding the fluorescence, an excitation light filter 23 allowing only the excitation light to pass therethrough, and a fluorescence filter 25 allowing only the fluorescence to pass therethrough. The insertion probe 9 is covered with a flexible outer sheath tube 9a in an area other than the distal end and is covered with a transparent outer sheath tube 9b at the distal end. The excitation light outgoing from the light guide 19 is reflected by the cone mirror 17 and is irradiated to the subject body 7 after passing through the transparent tube 9b. On the other hand, the fluorescence and the white light are reflected by the cone mirror 17 after passing through the transparent tube 9b and enter the image guide 21.

The cone mirror 17 is formed of a substantially conical member with a mirror provided on a conical surface thereof. The cone mirror 17 is arranged such that its center axis is substantially parallel to the center axis of the insertion probe 9. With such an arrangement, the cone mirror 17 reflects the excitation light outgoing from the light guide 19 along the center axis of the insertion probe 9 to advance in the radial direction of the insertion probe 9 and also reflects the fluorescence incoming in the radial direction of the insertion probe 9 to advance along the center axis of the insertion probe 9 and to enter the image guide 21.

The light guide 19 introduces the excitation light having passed through the half mirror 5 to the distal end of the insertion probe 9. An end surface 20 of the light guide 19 at the distal end side thereof functions as a light irradiating portion for irradiating the excitation light to the subject body 7 through the cone mirror 17. The light guide 19 is made up of a plurality of fiber bundles, and the excitation light filter 23 is disposed at the end surface (light irradiating and receiving portion) 20 of the light guide 19. The excitation light filter 23 is a filter allowing only the excitation light irradiated to the subject body 7 while cutting light having other wavelengths than that of the excitation light.

The image guide 21 introduces the fluorescence generated from the subject body 7 and the white light reflected by the subject body 7 to the half mirror 5. An end surface 22 of the image guide 21 at the distal end side thereof functions as a light receiving portion for receiving the fluorescence generated from the subject body 7. The image guide 21 is made up of a plurality of fiber bundles, and the fluorescence filter 25 is disposed at the end surface (light irradiating and receiving portion) 22 of the image guide 21. The fluorescence filter 25 is a filter allowing only the fluorescence generated from the subject body 7 and the white light reflected by the subject body 7 while cutting light having other wavelengths, in particular the excitation light. A focusing optical system 26 for focusing an image of the subject body 7 at the end surface 22 of the image guide 21 is disposed between the cone mirror 17 and the fluorescence filter 25.

Herein, the end surface 20 of the light guide 19 and the end surface 22 of the image guide 21 each serve as the light irradiating and receiving portion.

Returning to FIG. 1, the fluorescence detector 11 measures the intensity of fluorescence and outputs an electric signal depending on the measured fluorescence intensity. While a CCD (Charge Coupled Device) or a photoelectric transducer, for example, can be used as the fluorescence detector 11, the type of the fluorescence detector 11 is not limited to particular one.

The white light detector 11A measures the amount of the white light and outputs an electric signal depending on the measured amount of the white light. Similarly to the fluorescence detector 11, while a CCD or a photoelectric transducer, for example, can be used as the white light detector 11A, the type of the white light detector 11A is not limited to particular one.

The PC 13 extracts the lesion part T based on the output of the fluorescence detector 11 and controls the light source 3. The PC 13 comprises a lesion part extracting unit 27 (hereinafter referred to simply as an "extracting unit 27") for extracting the lesion part T, an image producing unit 29 for producing an image, and a control unit 31 for performing control to change the amount of the excitation light emitted from the light source 3. More specifically, the extracting unit 27 extracts the lesion part T based on the output of the fluorescence detector 11 and information regarding the amount of the excitation light, the information being obtained from the control unit 31. The image producing unit 29 produces, based on an output of the extracting unit 27, image data for displaying the lesion part T in different color from that of the other part. The control unit 31 controls the amount of the excitation light emitted from the light source 3.

The image combining unit 29A combines the image formed by the white light with the image of the extracted lesion part T. The electric signal representing the image formed by the white light is input to the image combining unit 29A from the white light detector 11A, and an electric signal representing the image of the extracted lesion part T is also input to the image combining unit 29A from the image producing unit 29. An electric signal representing the combined image is output from the image combining unit 29A to the monitor 15.

The monitor 15 displays the combined image input from the image combining unit 29A. In other words, data of the combined image produced by the image combining unit 29A (i.e., the electric signal representing the combined image) is input to the monitor 15.

An observation method (fluorescence determination method) using the endoscope device 1 having the above-described construction is summarized below.

First, as shown in FIG. 1, a medicament emitting fluorescence with irradiation of an excitation light is applied to the subject body 7. The medicament has a property of emitting stronger fluorescence when it is accumulated in the lesion part T, e.g., a tumor, in the subject body 7. After a time required for the medicament to sufficiently spread in the subject body 7 has lapsed from the application of the medicament to the subject body 7, observation using the endoscope device 1 is performed.

In a state where the distal end of the insertion probe 9 of the endoscope device 1 is arranged to locate in an observation area of the subject body 7, the control unit 31 controls the light source 3 to emit the excitation light from it. The excitation light emitted from the light source 3 enters the light guide 19 of the insertion probe 9. As shown in FIG. 2, the excitation light having entered the light guide 19 is guided to the distal end of the insertion probe 9 and exits the light guide 19 toward the cone mirror 17 after passing through the excitation light filter 23. The excitation light is reflected by the cone mirror 17 in the radial direction of the insertion probe 9 and is irradiated to the subject body 7 having passed through the transparent outer sheath tube 9b.

The applied medicament emits fluorescence from the subject body 7 irradiated by the excitation light. Herein, the intensity of the fluorescence generated from the medicament accumulated in the lesion part T of the subject body 7 is stronger than the intensity of the fluorescence generated from the medicament accumulated in the normal part N. Further, the intensity of the fluorescence generated from the medicament accumulated in a malignant tumor MT of the lesion part T is stronger than the intensity of the fluorescence generated from the medicament accumulated in a benign tumor BT.

More specifically, assuming that the intensity of the fluorescence generated from the normal part N is P1 and the intensity of the fluorescence generated from the lesion part T is P2, P1 and P2 can be expressed by the following formulae (1) and (2) using the amount P0 of the irradiated excitation light:

$$P1=(k/d2)P0 \quad (1)$$

$$P2=P0/d2+P0k/d2=\{(1+k)/d2\}P0 \quad (2)$$

In those formulae, d2 represents the observation distance, i.e., the distance from the insertion probe 9 to the subject body 7, and k represents the leakage coefficient of a leaked light.

As seen from the formulae (1) and (2), P1 and P2 are proportional to P0 under a condition that the observation distance d is constant.

The fluorescence generated from the subject body 7 and the white light reflected by the subject body 7 pass through the transparent outer sheath tube 9b in the radial direction of the insertion probe 9 and advance toward the cone mirror 17. The fluorescence and the white light having reached the cone mirror 17 are reflected by it to advance in the direction of the center axis of the insertion probe 9. The reflected fluorescence and white light are focused by the focusing optical system onto the end surface 22 of the image guide 21. The fluorescence and the white light both focused by the focusing optical system pass through the fluorescence filter 25 and then enter the image guide 21. The fluorescence and the white light having entered the image guide 21 are guided externally of the subject body 7 to advance toward the half mirror 5. Of the fluorescence and the white light incident upon the half mirror 5, the fluorescence passes through the half mirror 5 and comes into the fluorescence detector 11. The incoming fluorescence focuses an image of the subject body 7 on the plane of light incidence of the fluorescence detector 11. The fluorescence detector 11 outputs an electric signal depending on the intensity of the focused fluorescence to the extracting unit 27. On the other hand, the white light is reflected by the half mirror 5 toward the white light detector 11A and comes into the white light detector 11A. The incoming white light focuses an image of the subject body 7 on the plane of light incidence of the white light detector 11A. The white light detector 11A outputs an electric signal depending on the amount of the focused white light to the image combining unit 29A.

The extracting unit 27 extracts the lesion part T (including the benign tumor BT and the malignant tumor MT) based on both the electric signal input from the fluorescence detector 11 and the electric signal regarding the amount of the excitation light, which is input from the control unit 31, and then outputs the extracted result to the image producing unit 29. The image producing unit 29 produces, based on the output of the extracting unit 27, image data for displaying the benign tumor BT and the malignant tumor MT in respective different colors from the other portion, and then outputs the produced image data to the image combining unit 29A. The image combining unit 29A produces, based on the electric signal input from the white light detector 11A and the image data (electric signal) input from the image producing unit 29, a combined image of the image formed by the white light and the image of the extracted lesion part T, and then outputs image data representing the combined image to the monitor 15. Based on the input image data, the monitor 15 displays a fluorescence image I1 and a white light image I2 of the subject body 7 while the benign tumor BT and the malignant tumor MT are displayed in respective different colors from the other portion.

A method of extracting the lesion part T, which includes the benign tumor BT and the malignant tumor MT, according to the feature of the first embodiment will be described below.

Figure 3:
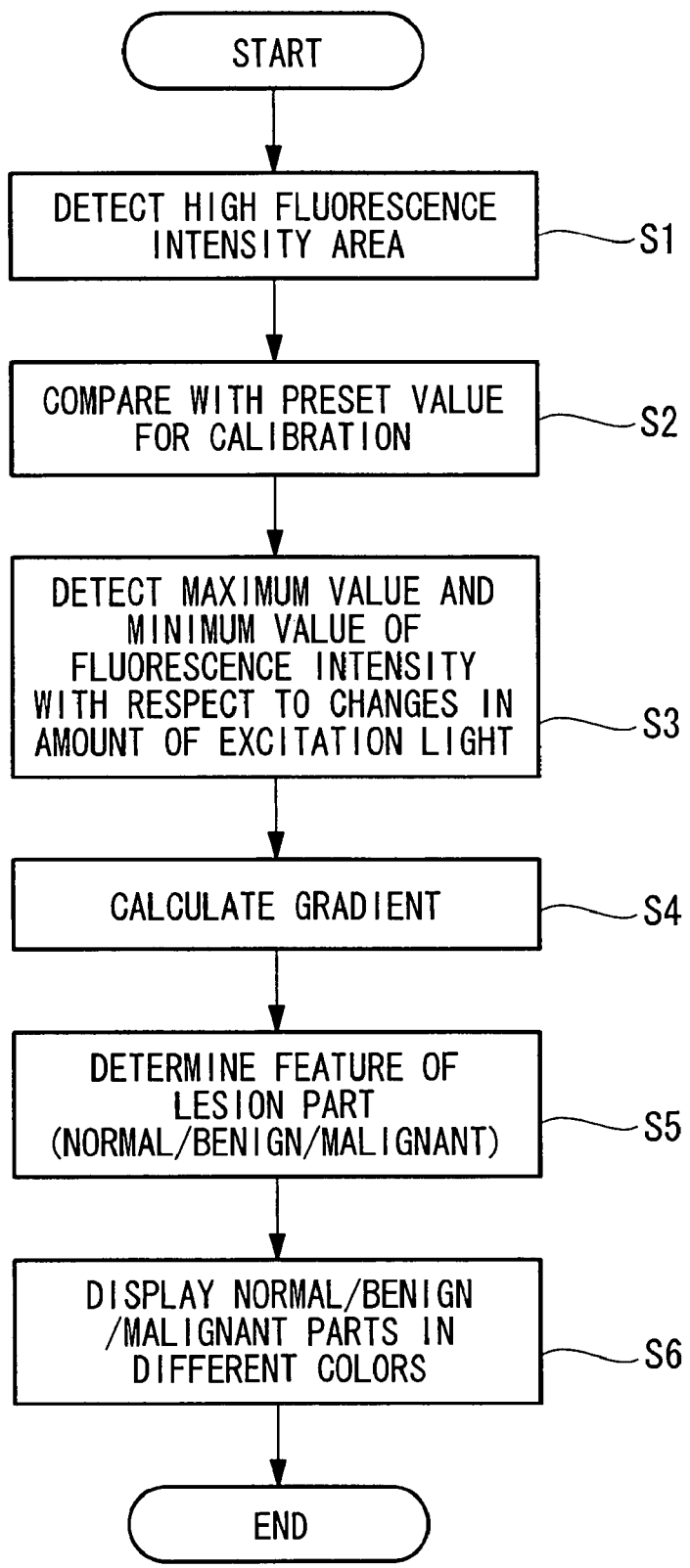
FIG. 3 is a flowchart for explaining a method of extracting a lesion part in the endoscope device shown in FIG. 1.

FIG. 3 is a flowchart for explaining the method of extracting the lesion part T in the endoscope device 1 shown in FIG. 1.

First, as shown in FIG. 3, a high fluorescence intensity area in which the fluorescence intensity is high is extracted from the observation area of the subject body 7 (step S1). As described above with reference to FIG. 1, the control unit 31 outputs the control signal to the light source 3 for emitting the excitation light in predetermined amount from the light source 3. When the excitation light is irradiated to the subject body 7, fluorescence is emitted from the normal part N and the lesion part T in the subject body 7. A fluorescence image of the subject body 7 is focused on the plane of light incidence of the fluorescence detector 11, and an electric signal depending on the fluorescence intensity of the focused image is input to the extracting unit 27 from the fluorescence detector 11. Based on the input electric signal, the extracting unit 27 detects the high fluorescence intensity area in which the intensity of the fluorescence generated from the subject body 7 is high (detecting step).

As described above, the high fluorescence intensity area in which the fluorescence intensity is high represents an area of the lesion part T, i.e., an area of the benign tumor BT or the malignant tumor MT, with a high probability.

Next, as shown in FIG. 3, the fluorescence intensity in the high fluorescence intensity area is compared with a preset value to perform calibration (step S2). In other words, as shown in FIG. 1, the extracting unit 27 extracts the fluorescence intensity in the detected high fluorescence intensity area and compares it with a preset value of the fluorescence intensity, which is previously set in the PC 13, for the purpose of calibration.

Figure 4:
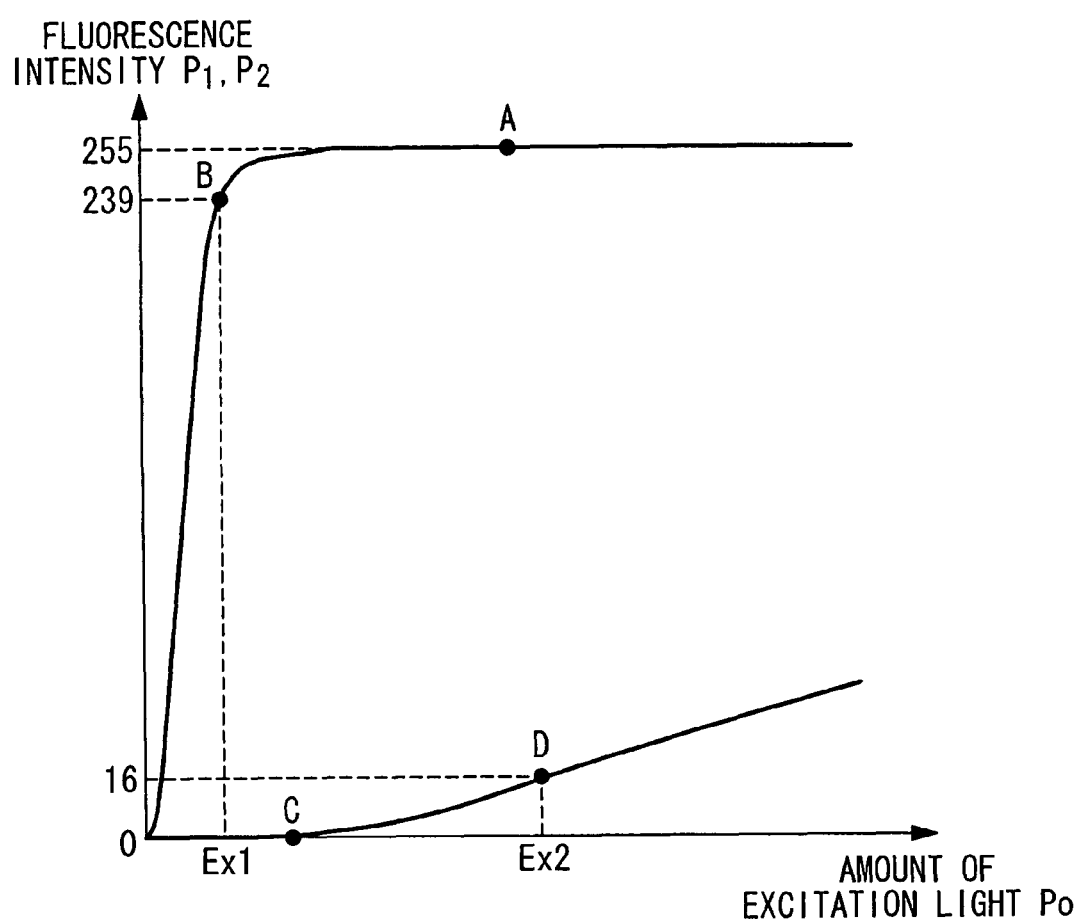
FIG. 4 is a graph for explaining a method of calibrating the fluorescence intensity in the first embodiment.

FIG. 4 is a graph for explaining a method of calibrating the fluorescence intensity in the first embodiment.

When the fluorescence intensity in the high fluorescence intensity area is, for example, in the stage 255 of 256 stages ranging from 0 to 255, i.e., in a saturated state, as indicated by a point A in FIG. 4, linearity of the fluorescence intensity with respect to the amount of the excitation light is not ensured in some cases. Therefore, calibration is performed by previously setting an amount Ex1 of the excitation light corresponding to a maximum value of the fluorescence intensity when the fluorescence intensity is at a maximum level within a linear zone, e.g., when the fluorescence intensity is in the stage 239, in the PC 13 as indicated by a point B in FIG. 4, and by reducing the amount of the excitation light to Ex1.

On the other hand, when the fluorescence intensity in the high fluorescence intensity area is, for example, in the stage 0, i.e., in a state where fluorescence cannot be detected with the detection sensitivity of the extracting unit 27, as indicated by a point C in FIG. 4, linearity of the fluorescence intensity with respect to the amount of the excitation light is also not ensured in some cases. Therefore, calibration is performed by previously setting an amount Ex2 of the excitation light corresponding to a minimum value of the fluorescence intensity which can be detected with the detection sensitivity of the extracting unit 27, e.g., when the fluorescence intensity is in the stage 16, in the PC 13 as indicated by a point D in FIG. 4, and by increasing the amount of the excitation light to Ex2.

Notice that the stages of the fluorescence intensity selected for the calibration are mentioned above merely by way of example, and are not limited to the above-mentioned ones.

Figure 5:
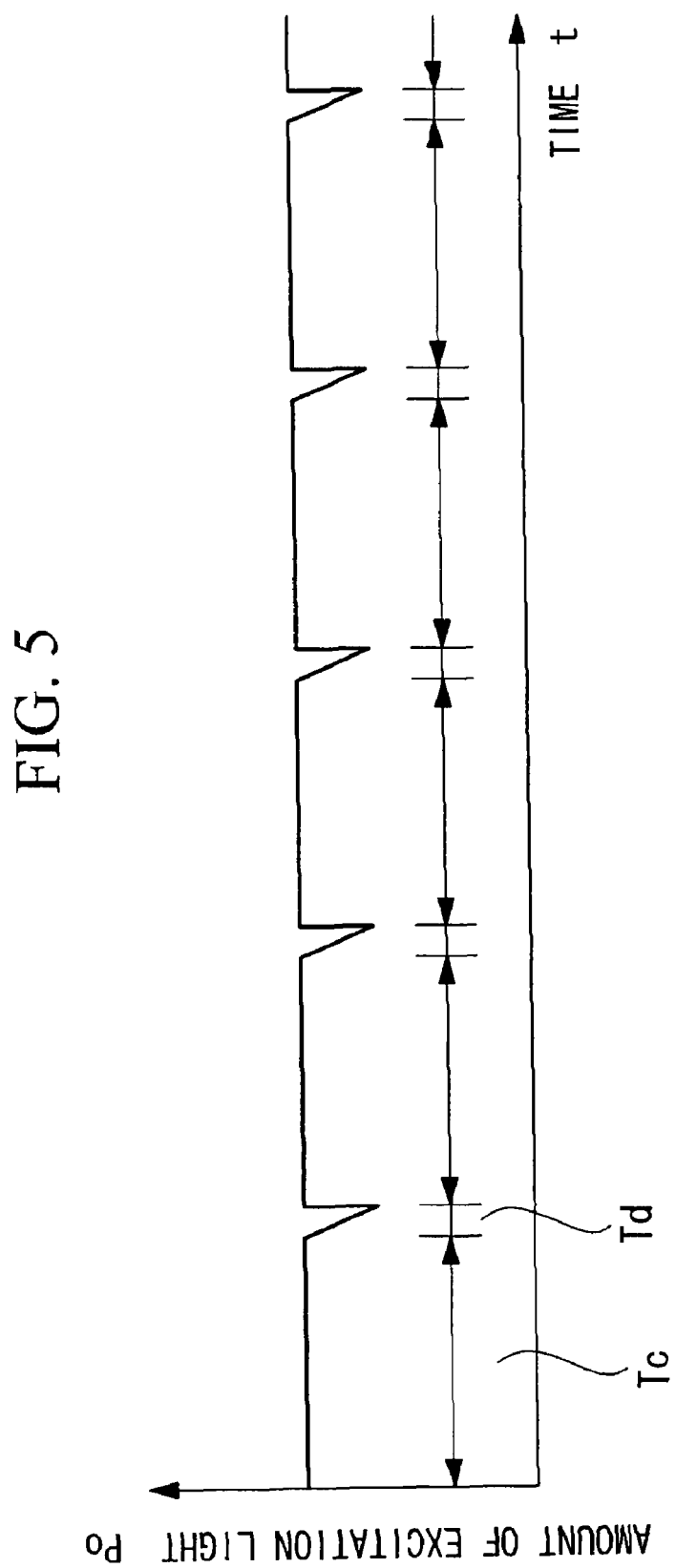
FIG. 5 is a chart for explaining changes in the amount of an excitation light over time, which is emitted from a light source in FIG. 1.

FIG. 5 is a chart for explaining changes in the amount of the excitation light over time, which is emitted from the light source in FIG. 1.

After completion of the comparative calibration, the control unit 31 changes the amount of the excitation light, and the extracting unit 27 extracts the lesion part T of the subject body 7 based on relationships between measured values of changes in the fluorescence intensity with respect to changes in the amount of the excitation light and information regarding the changes in the amount of the excitation light, the information being obtained from the control unit 31. More specifically, as shown in FIG. 3, a maximum value and a minimum value of the fluorescence intensity in the high fluorescence intensity area are measured with respect to the changes in the amount of the excitation light (step S3). To that end, as shown in FIG. 1, the control unit 31 outputs the control signal to the light source 3 such that the light source 3 emits the excitation light in amount changing over time (light amount changing step, distance holding step, and light irradiating and receiving step). A light amount change pattern is set, as shown in FIG. 5, to a pattern comprising a constant period Tc (e.g., 0.9 sec) in which the light amount is constant, and a change period Td (e.g., 0.1 sec) in which the light amount is reduced with the lapse of time. The constant period Tc in which the light amount is constant may be set in match with the above-described irradiating step, and it is not limited to particular one. In the change period Td, because the amount of the excitation light is reduced with the lapse of time, the amount of the fluorescence generated from the subject body 7 is also reduced. Based on changes in the fluorescence intensity in the high fluorescence intensity area during the change period Td, the extracting unit 27 measures the maximum value and the minimum value of the fluorescence intensity (fluorescence intensity measuring step).

A ratio of the constant period Tc to the change period Td can be set to a certain desired value, and it is not limited to a particular value.

After completing the measurement of the maximum value and the minimum value of the fluorescence intensity, as shown in FIG. 3, a gradient of the changes in the fluorescence intensity is calculated (step S4). More specifically, as shown in FIG. 6, the extracting unit 27 calculates a gradient of the changes in the fluorescence intensity based on the maximum value and the minimum value of the fluorescence intensity, as well as the respective amounts of the excitation light at the maximum value and the minimum value of the fluorescence intensity (extracting step).

Figure 6:
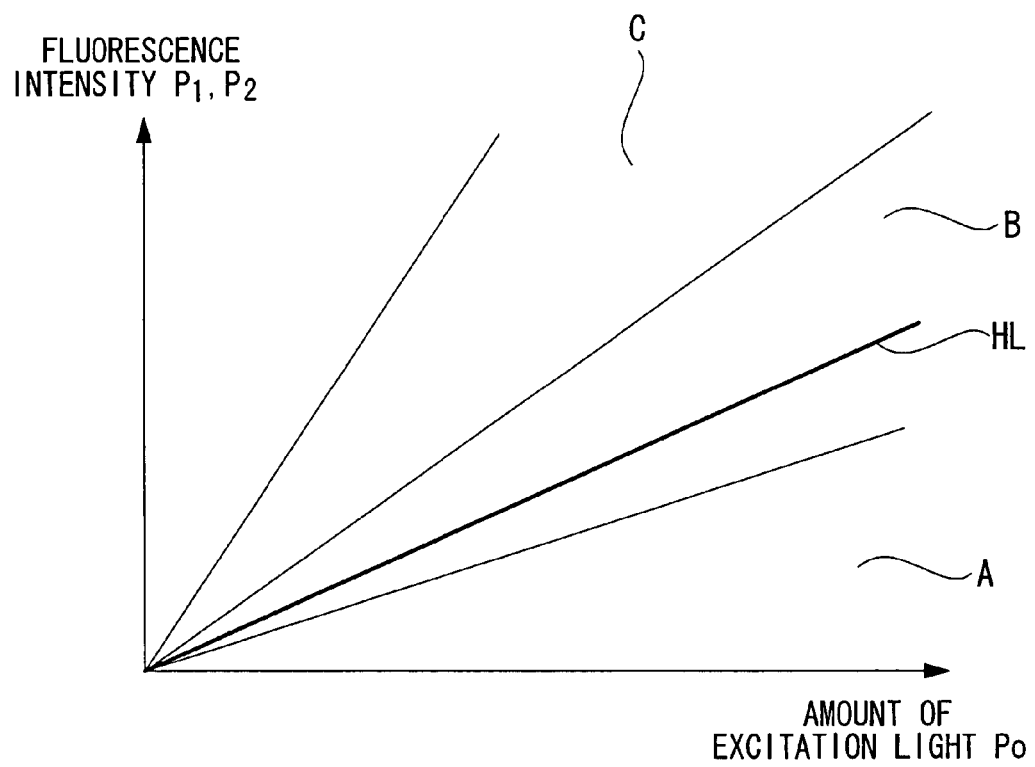
FIG. 6 is a graph for explaining the relationship between the amount of the excitation light and the fluorescence intensity.

FIG. 6 is a graph for explaining the relationship between the amount of the excitation light and the fluorescence intensity.

After the gradient of the changes in the fluorescence intensity has been calculated, as shown in FIG. 3, a feature of the high fluorescence intensity area is determined (step S5). The gradient of the changes in the fluorescence intensity calculated in step S4 is used to determine the feature. More specifically, the gradient (rate) of the changes in the fluorescence intensity in the lesion part T with respect to the changes in the amount of the excitation light is greater than that in the normal part N. Further, the gradient (rate) of the changes in the fluorescence intensity in the malignant tumor MT of the lesion part T with respect to the changes in the amount of the excitation light is greater than that in the normal part N. In practice, as seen from the above-mentioned formulae (1) and (2), the gradient (rate) of the changes in the fluorescence intensity in the lesion part T with respect to the changes in the amount of the excitation light is greater than that in the normal part N. By utilizing such a characteristic, it is determined based on the gradient of the changes in the fluorescence intensity whether the high fluorescence intensity area is the normal part N or the lesion part T (including the benign tumor BT and the malignant tumor MT).

Data of the graph, shown in FIG. 6, is previously stored in the extracting unit 27. By comparing the calculated gradient of the changes in the fluorescence intensity in the high fluorescence intensity area with the previously stored data, the extracting unit 27 determines whether the high fluorescence intensity area is the normal part N or the lesion part T (including the benign tumor BT and the malignant tumor MT). In FIG. 6, the horizontal axis represents the amount of the excitation light irradiated to the subject body 7, and the vertical axis represents the intensity of the fluorescence generated from the subject body 7. Further, in the graph of FIG. 6, an area A indicates an area covering the gradient of the changes in the intensity of the fluorescence generated from the normal part N, an area B indicates an area covering the gradient of the changes in the intensity of the fluorescence generated from the benign tumor BT of the lesion part T, and an area C indicates an area covering the gradient of the changes in the intensity of the fluorescence generated from the malignant tumor MT of the lesion part T. In this first embodiment, the description is made of the case where, as indicated by a fat solid line HL, the gradient of the changes in the intensity of the fluorescence generated from the high fluorescence intensity area represents the benign tumor BT.

After the determination of the high fluorescence intensity area, as shown in FIG. 3, the high fluorescence intensity area is displayed in a color-coded manner (step S6). As described above with reference to FIG. 1, the extracting unit 27 outputs the result of determining the high fluorescence intensity area to the image producing unit 29. Based on the determination result, the image producing unit 29 produces image data of the subject body 7 which represents the high fluorescence intensity area in a color-coded manner. The color-coding is set so as to discriminate the normal part N, the benign tumor BT, and the malignant tumor MT from one another. The image data produced by the image producing unit 29 is output to the monitor 15 and is displayed on the monitor 15.

The monitor 15 displays an image only during the constant period Tc shown in FIG. 5 and does not display an image during the change period Td.

With the arrangement described above, since the endoscope device 1 includes the light source 3 for emitting the excitation light to excite fluorescence, the control unit 31 for controlling the amount of the excitation light, and the extracting unit 27 for extracting the lesion part T based on changes in the fluorescence intensity, the benign tumor BT and the malignant tumor MT of the lesion part T in the subject body 7 can be easily determined. The light source 3 can change the amount of the excitation light, which is emitted from the light source 3, under control of the control unit 31. The fluorescence detector 11 can measure the intensity of the fluorescence generated with irradiation of the excitation light and hence to measure changes in the fluorescence intensity that varies depending on changes in the amount of the excitation light. Based on the measured changes in the fluorescence intensity, the extracting unit 27 can extract the benign tumor BT and the malignant tumor MT of the lesion part T from the normal part N of the subject body 7. More specifically, by utilizing such a characteristic that the intensities of the fluorescences generated from the normal part N and the benign tumor BT and the malignant tumor MT of the lesion part T change in different ways with respect to changes in the amount of the irradiated excitation light, the extracting unit 27 is able to extract the benign tumor BT and the malignant tumor MT of the lesion part T from the normal part N. Thus, since the extracting unit 27 extracts the benign tumor BT and the malignant tumor MT of the lesion part T based on the changes in the fluorescence intensity, the lesion part T can be more easily determined with a smaller volume of information to be processed in comparison with the method of extracting the lesion part T by analyzing a fluorescence spectrum.

In particular, since the extracting unit 27 extracts the lesion part T based on the ratio of the amount of the excitation light to the fluorescence intensity, i.e., the gradient of the changes in the fluorescence intensity with respect to the changes in the amount of the excitation light, it is possible to easily determine the lesion part T of the subject body 7. Also, because of extracting the lesion part T based on the gradient of the changes in the fluorescence intensity with respect to the changes in the amount of the excitation light, the extracting unit 27 can more precisely extract the lesion part T in comparison with the method not based on the amount of the excitation light. Stated another way, since the extracting unit 27 employs, for the extraction of the lesion part T, only the changes in the fluorescence intensity which are caused depending on the changes in the amount of the excitation light, the unit 27 can precisely extract the benign tumor BT and the malignant tumor MT of the lesion part T in the subject body 7.

Since the cone mirror 17 is disposed at the distal end of the insertion probe 9, the distance between the subject body 7 and the end surface 20 and the distance between the subject body 7 and the end surface 22 can be each held at a predetermined constant value, thus enabling the lesion part T in the subject body 7 to be easily determined.

Since the cone mirror 17 serves to hold constant the respective distances from the end surface 20 and the end surface 22 to the subject body 7, i.e., the respective distances from the end surface 20 and the end surface 22 to each of the normal part N, the benign tumor BT of the lesion part T, and the malignant tumor MT of the lesion part T, the excitation lights irradiated to the normal part N, the benign tumor BT of the lesion part T, and the malignant tumor MT of the lesion part T and the fluorescences generated from the normal part N, the benign tumor BT of the lesion part T, and the malignant tumor MT of the lesion part T are attenuated substantially at an equal rate. Therefore, the extracting unit 27 can easily discriminate the differences among the changes in the intensities of the fluorescences generated from the normal part N, the benign tumor BT of the lesion part T, and the malignant tumor MT of the lesion part T.

Since the endoscope device 1 includes the image producing unit 29 for producing an image based on the output of the extracting unit 27 and the monitor 15 for displaying the produced image, the lesion part T can be confirmed on the displayed image and the determination of the lesion part T in the subject body 7 can be easily performed.

Since the image producing unit 29 produces an image based on the output of the extracting unit 27, the unit 29 can produce an image that ensures easy confirmation of the lesion part T. Since the monitor 15 displays the image produced by the image producing unit 29, it is possible for, e.g., an operator of the endoscope device 1 to easily recognize, e.g., the shape of the lesion part T and to easily determine the lesion part T.

Since the control unit 31 controls repeatedly the constant period in which the amount of the excitation light is constant and the change period in which the amount of the excitation light is changed, an image can be displayed in such a manner that it is easier to view, while enabling the lesion part T to be extracted. Further, with the presence of the constant period in which the amount of the excitation light is constant, an image being easier to view can be displayed on the display unit and the determination of the lesion part T can be more easily made in comparison with the method of continuously changing the amount of the excitation light.

Since the monitor 15 displays the image when the amount of the excitation light is constant and does not display the image when the amount of the excitation light is changed, an image having constant brightness and being easy to view can be displayed. More specifically, since the monitor 15 displays the image when the amount of the excitation light is constant, an image having constant and stable brightness and being easy to view can be displayed to the operator of the endoscope device 1. On the other hand, since the monitor 15 does not display the image when the amount of the excitation light is changed, display of an image can be avoided which has varying brightness and is hard to view. Accordingly, the operator can determine the lesion part T based on the image which is easy to view.

The provision of the excitation light filter 23 enables only the excitation light to be irradiated to the subject body 7. It is therefore possible to prevent fluorescence from being generated from the subject body 7 with irradiation of other light than the excitation light, and to precisely discriminate the lesion part T.

The provision of the fluorescence filter 25 enables only the fluorescence to enter the fluorescence detector 11. It is therefore possible to prevent other light than the fluorescence from entering the fluorescence detector 11, and to precisely discriminate the lesion part T.

The observation method using the endoscope device 1 of the first embodiment can easily discriminate the lesion part T by measuring a maximum value and a minimum value of the fluorescence intensity while changing the amount of the excitation light (step S3), and determining the presence or absence of the lesion part T based on the maximum value and the minimum value of the fluorescence intensity (steps S4 and S5). The intensities of the fluorescences generated from the normal part N and the benign tumor BT and the malignant tumor MT of the lesion part T change in different ways with respect to changes in the amount of the irradiated excitation light. Therefore, when the same excitation light is irradiated while changing its amount, the maximum value and the minimum value of the intensity of the fluorescence generated from the normal part N differ respectively from the maximum value and the minimum value of the intensity of the fluorescence generated from the lesion part T. Accordingly, based on the differences in the maximum value and the minimum value of the fluorescence intensity, whether the lesion part T is present in the subject body 7 or not can be easily determined in steps S4 and S5.

Prior to measuring the maximum value and the minimum value of the fluorescence intensity (step S3), the excitation light is irradiated to the subject body 7 for detecting the high fluorescence intensity area in which the fluorescence intensity is high, from the subject body 7 generating the fluorescence (step S1). In step S3, therefore, the maximum value and the minimum value of the fluorescence intensity in the high fluorescence intensity area can be detected, thus enabling the lesion part T to be easily discriminated.

When the excitation light is irradiated in the same amount, the intensity of the fluorescence generated from the lesion part T is stronger than that generated from the normal part N. Based on the difference between the intensity of the fluorescence generated from the normal part N and the intensity of the fluorescence generated from the lesion part T, therefore, the extracting unit 27 can extract the high fluorescence intensity area which is possibly the lesion part T. Further, by executing steps S3 to S5 in the high fluorescence intensity area which is possibly the lesion part T, the presence or absence of the lesion part T in the high fluorescence intensity area can be determined, thus enabling the lesion part T to be easily discriminated.

During the change period Td, the amount of the excitation light can be reduced with the lapse of time as described above. However, the method of changing the amount of the excitation light is not limited to particular one, and the amount of the excitation light may be changed to increase with the lapse of time.

Additionally, while the display unit is described above as not displaying the image during the change period Td, a display mode is not limited to particular one and the display unit may display the image during the change period Td. When displaying the image during the change period Td, the display unit may display the image data produced by the image producing unit 29, as it is, during the change period Td as well, or may display the image immediately before the change period Td in a continuous manner. Further, the steps of, e.g., extracting the lesion part T in the extracting unit 27 may be performed as a background process, and a resulting image may be displayed on the display unit.

Figure 7:
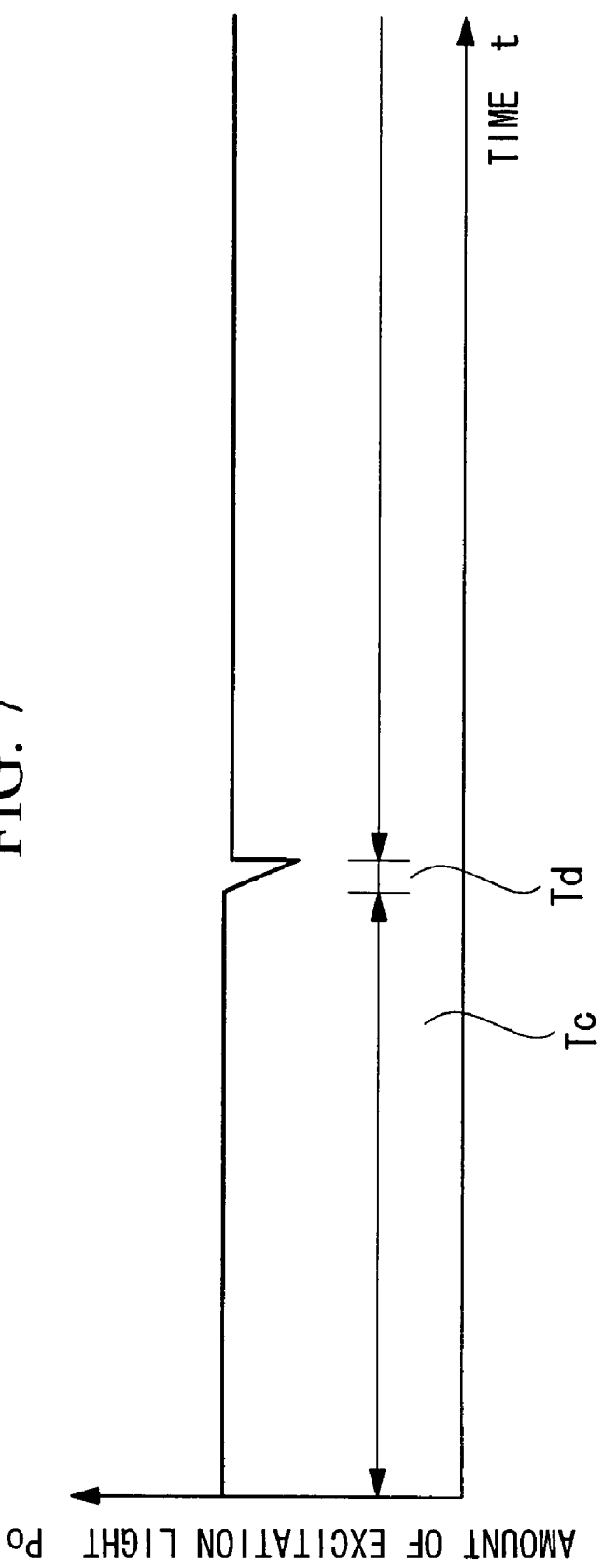
FIG. 7 is a chart for explaining another example of changes in the amount of the excitation light over time, which is emitted from the light source in FIG. 1.

FIG. 7 is a chart for explaining another example of changes in the amount of the excitation light over time, which is emitted from the light source in FIG. 1.

While the pattern for changing the amount of the excitation light emitted from the light source 3 is set to periodically change the light amount in FIG. 5, the amount of the excitation light may be changed at predetermined timing as shown in FIG. 7. The predetermined timing can be set, for example, in accordance with an instruction from the operator.

In such a case, as a basic principle, the control unit 31 controls the light source 3 to continuously emit the excitation light in constant amount. At the predetermined timing in accordance with an instruction from the operator, for example, the control unit 31 changes the amount of the excitation light emitted from the light source 3. The extracting unit 27 extracts the lesion part T at the timing at which the amount of the excitation light is changed.

The control method of this example is advantageous in increasing flexibility in selection of the timing at which the extraction of the lesion part T is performed, and in enabling the lesion part T to be more easily determined in comparison with the above-described method of cyclically repeating the constant period Tc in which the amount of the excitation light is constant and the change period Td in which the amount of the excitation light is changed.

Figure 8:
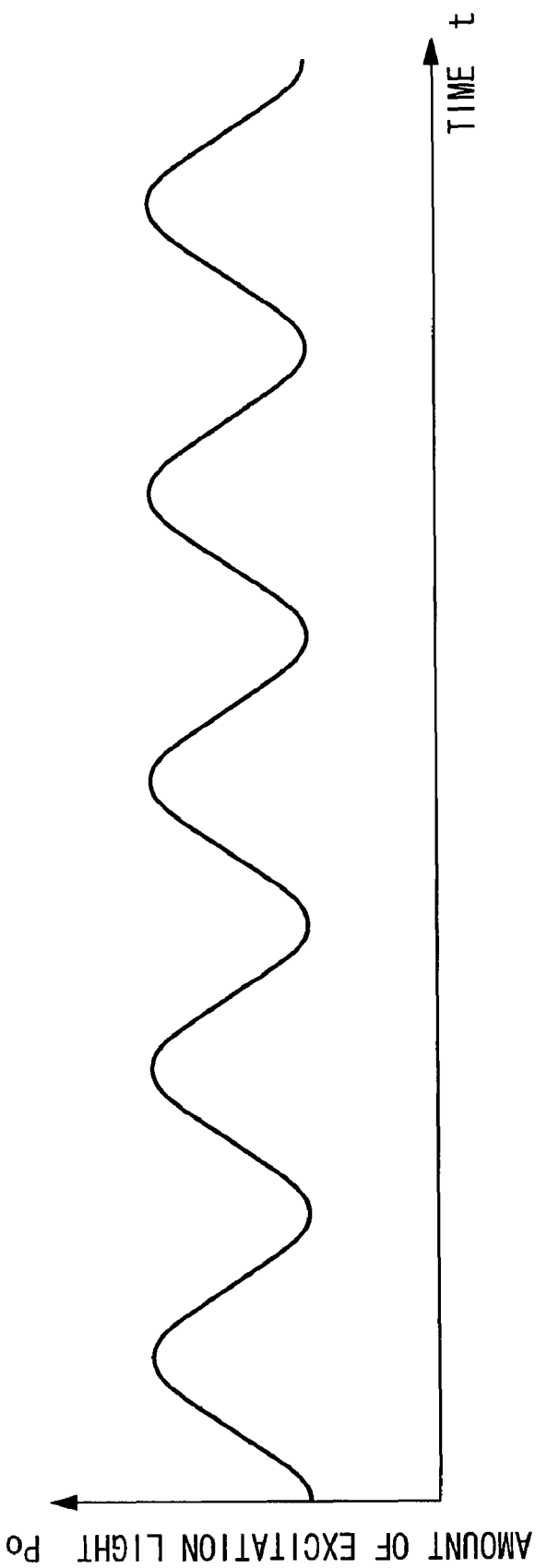
FIG. 8 is a chart for explaining still another example of changes in the amount of the excitation light over time, which is emitted from the light source in FIG. 1.

FIG. 8 is a chart for explaining still another example of changes in the amount of the excitation light over time, which is emitted from the light source in FIG. 1.

While the pattern for changing the amount of the excitation light emitted from the light source 3 is set to periodically change the light amount in FIG. 5, the amount of the excitation light may be changed continuously as shown in FIG. 8.

In such a case, the control unit 31 controls the light source 3 to emit the excitation light in continuously changing amount. The image producing unit 29 can produce the image data at predetermined timing and can display the image on the monitor 15 at the predetermined timing.

The control method of this example is advantageous in always allowing the extraction of the lesion part T to be performed and in enabling the lesion part T to be more easily determined in comparison with the above-described method of cyclically providing the constant period Tc in which the amount of the excitation light is constant.

Figure 9:
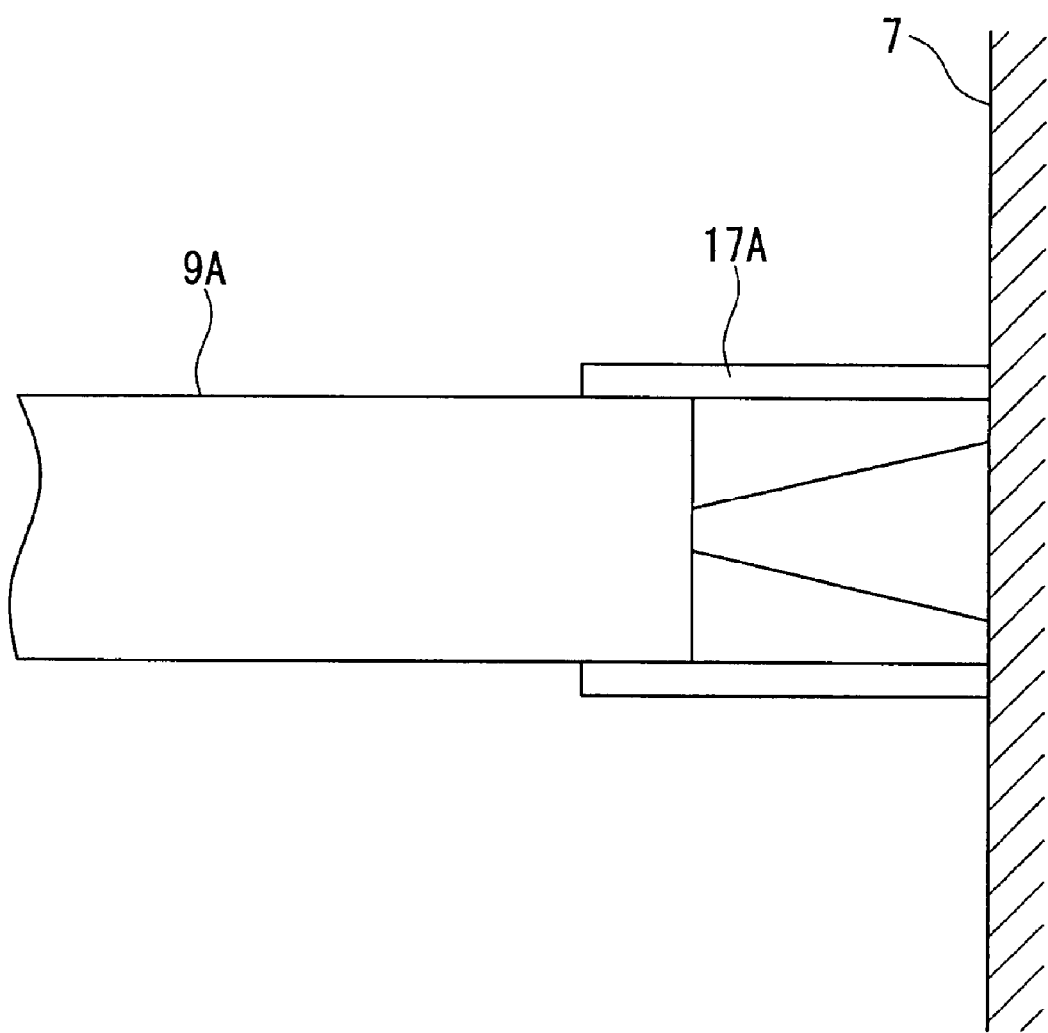
FIG. 9 is a schematic view for explaining another structure of the inserted-side end portion of the endoscope device shown in FIG. 1.

FIG. 9 is a schematic view for explaining another structure of the inserted-side end portion of the endoscope device shown in FIG. 1.

While in the above description the distance between the light source 3 and the subject body 7 is held constant by using the insertion probe 9 of the laterally-viewing type including the cone mirror 17, the arrangement for holding that distance constant is not limited to particular one. For example, as shown in FIG. 9, the distance between the light source 3 and the subject body 7 may be held constant by arranging a cap (distance holding member) 17A at the tip of an insertion probe 9A of the straightly-viewing type.

[Second Embodiment]

An endoscope device according to a second embodiment of the present invention will be described below with reference to FIGS. 10-12.

The endoscope device of this second embodiment has a basic construction similar to that of the first embodiment, but it differs from the first embodiment in construction of the light source, etc. and the observation method. Therefore, the following description of this second embodiment is made of primarily the light source, etc. and the observation method with reference to FIGS. 10-12, while a description of the insertion probe, etc. is omitted.

Figure 10:
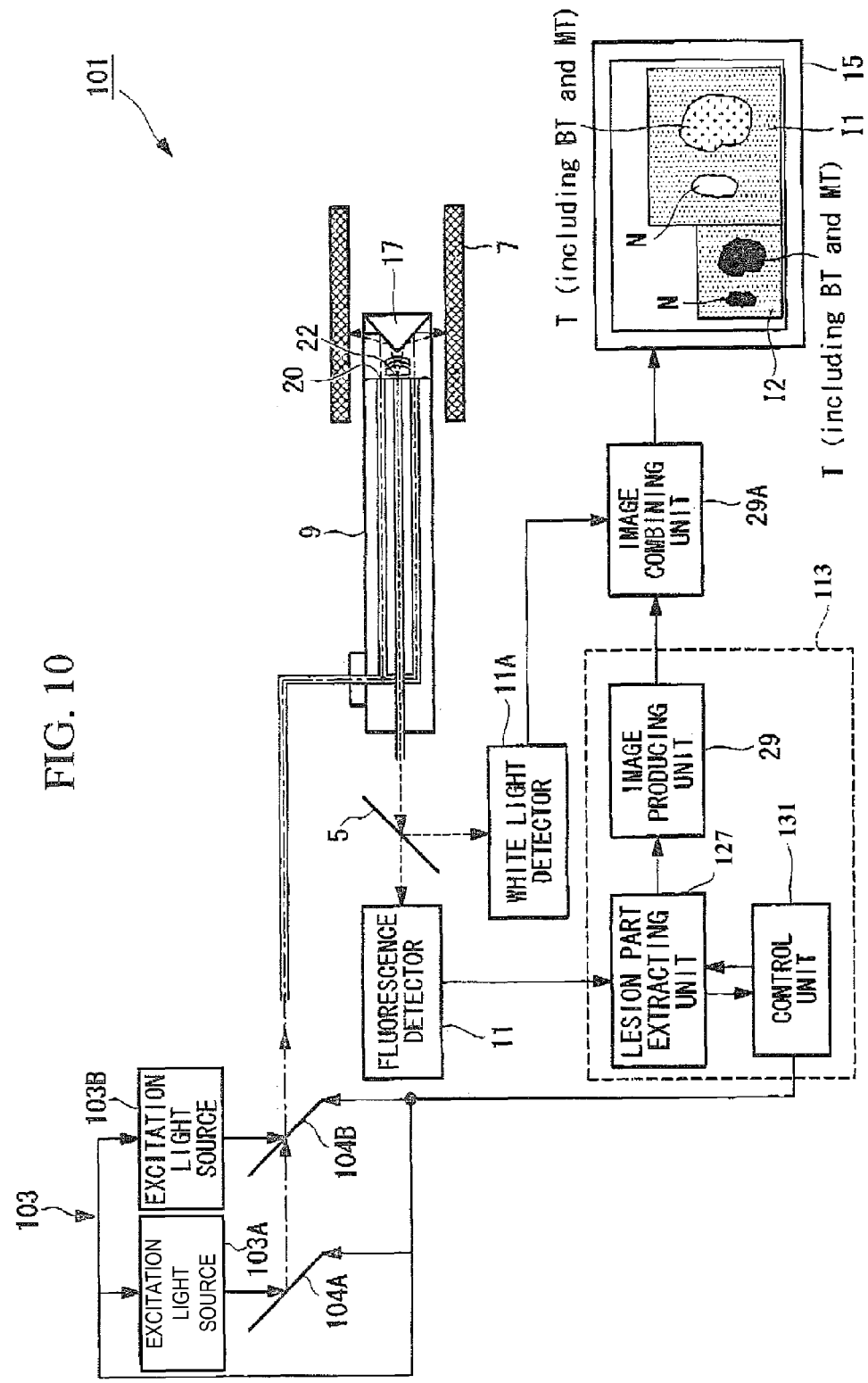
FIG. 10 is a block diagram for explaining a general construction of an endoscope device according to a second embodiment of the present invention.

FIG. 10 is a block diagram for explaining a general construction of the endoscope device according to the second embodiment.

Note that the same components as those in the first embodiment are denoted by the same reference numerals and a description of those components is omitted.

An endoscope device (lesion extracting device) 101 comprises, as shown in FIG. 10, a light source 103 for emitting an excitation light, a half mirror 5 allowing fluorescence to pass therethrough and reflecting a white light, an insertion probe 9 which is inserted into a subject body 7 to be examined, a fluorescence detector 11 for measuring fluorescence, a white light detector 11A for detecting a white light, a PC 113 for performing, e.g., extraction of a lesion part T, an image combining unit 29A for combining an image formed by the white light with an image of the extracted lesion part T, and a monitor 15 for displaying the combined image.

The light source 103 emits the excitation light irradiated to the subject body 7. The light source 103 comprises an excitation light source 103A for emitting an excitation light with a wavelength of λA (one wavelength), an excitation light source 103B for emitting an excitation light with a wavelength of AB (another wavelength), a reflecting member 104A for reflecting the excitation light emitted from the excitation light source 103A, and a reflecting member 104B for reflecting the excitation light emitted from the excitation light source 103B. Control signals from a control unit 131 in the PC 113 are input to the excitation light sources 103A and 103B, and the excitation light sources 103A and 103B change the amounts of the excitation lights emitted from them in accordance with the control signals. Also, the reflection of the excitation lights by the reflecting members 104A and 104B is controlled in accordance with control signals input from the control unit 131 to the reflecting members 104A and 104B. The reflecting members 104A and 104B serve to reflect the respective excitation lights emitted from the excitation light sources 103A and 103B toward the insertion probe 9.

The PC 113 extracts the lesion part T based on an output of the fluorescence detector 11 and controls the light source 103. The PC 113 comprises an extracting unit 127 for extracting the lesion part T, an image producing unit 29 for producing an image, and a control unit 131 for performing control to change the wavelengths and the amounts of the excitation lights emitted from the light source 103. More specifically, the extracting unit 127 extracts the lesion part T based on the output of the fluorescence detector 11 and information regarding the amounts of the excitation lights. The control unit 131 controls the wavelengths and the amounts of the excitation lights emitted from the light source 103.

An observation method (fluorescence determination method) using the endoscope device 101 having the above-described construction is summarized below.

First, as shown in FIG. 10, a medicament emitting fluorescence with irradiation of an excitation light is applied to the subject body 7. The medicament has a property of emitting stronger fluorescence when it is accumulated in the lesion part T, e.g., a tumor, in the subject body 7. After a time required for the medicament to sufficiently spread in the subject body 7 has lapsed from the application of the medicament to the subject body 7, observation using the endoscope device 101 is performed.

In a state where the distal end of the insertion probe 9 of the endoscope device 101 is arranged to locate in an observation area of the subject body 7, the control unit 131 emits the excitation light from the light source 103. The excitation light emitted from the light source 3 is irradiated to the subject body 7 through the insertion probe 9.

The applied medicament emits fluorescence from the subject body 7 irradiated by the excitation light. As in the first embodiment, the intensity of the fluorescence generated from the subject body 7 is weakest when the fluorescence is generated from the normal part N, and is increased in the order of the fluorescence generated from the benign tumor BT of the lesion part T and the fluorescence generated from the malignant tumor MT of the lesion part T.

The fluorescence generated from the subject body 7 and the white light reflected by the subject body 7 are introduced to the half mirror 5 through the insertion probe 9. Of the fluorescence and the white light incident upon the half mirror 5, the fluorescence passes through the half mirror 5 and comes into the fluorescence detector 11. The fluorescence detector 11 outputs an electric signal depending on the intensity of the incoming fluorescence as in the first embodiment. On the other hand, the white light is reflected by the half mirror 5 toward the white light detector 11A and comes into the white light detector 11A. The white light detector 11A outputs an electric signal depending on the amount of the incoming white light as in the first embodiment.

The extracting unit 127 extracts the lesion part T (including the benign tumor BT and the malignant tumor MT) based on both the electric signal input from the fluorescence detector 11 and the electric signal regarding the amount of the excitation light, which is input from the control unit 131. As in the first embodiment, the image producing unit 29 produces, based on the output of the extracting unit 127, image data for displaying the benign tumor BT and the malignant tumor MT in respective different colors from the other portion.

A method of extracting the lesion part T, which includes the benign tumor BT and the malignant tumor MT, according to the feature of the second embodiment, will be described below.

Figure 11:
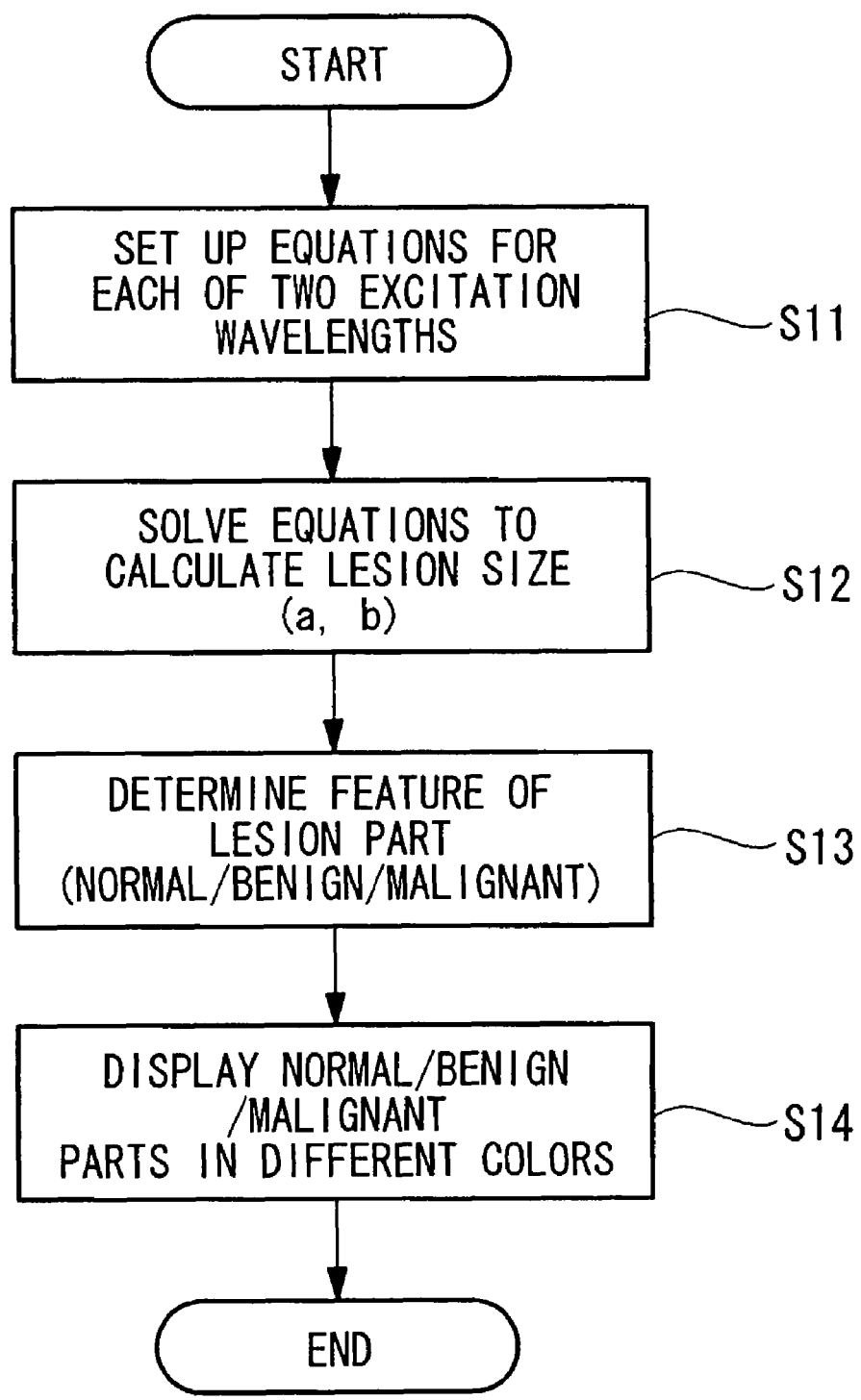
FIG. 11 is a flowchart for explaining a method of extracting a lesion part in the endoscope device shown in FIG. 10.

FIG. 11 is a flowchart for explaining the method of extracting the lesion part T in the endoscope device 101 shown in FIG. 10.

First, as shown in FIG. 11, equations are derived based on the amounts of the excitation lights having two different wavelengths and the intensities of the respective fluorescences generated from the subject body 7 corresponding to the two excitation lights (calculation preparatory step) (step S11). As shown in FIG. 10, the control unit 131 outputs the control signal to the light source 103 for emitting the excitation light in one amount PA0 from, e.g., the excitation light source 103A. When the excitation light is irradiated to the subject body 7, fluorescence (one kind of fluorescence) is emitted from the normal part N and the lesion part T (fluorescence generating area) of the subject body 7. A fluorescence image of the subject body 7 is focused on the plane of light incidence of the fluorescence detector 11, and an electric signal depending on the fluorescence intensity PA1 of the focused image is input to the extracting unit 127 from the fluorescence detector 11 (first measuring step).

Then, the control unit 131 controls the light source 103 to emit the excitation light in one amount PB0 from the excitation light source 103B. The fluorescence detector 11 outputs an electric signal depending on the intensity PB1 of fluorescence (another kind of fluorescence) generated with irradiation of the excitation light at that time, and the electric signal is input to the extracting unit 127 (second measuring step).

Further, the control unit 131 controls the light source 103 to emit the excitation light in another amount PC0 from the excitation light source 103B. The fluorescence detector 11 outputs an electric signal depending on the intensity PC1 of fluorescence (another kind of fluorescence) generated with irradiation of the excitation light at that time, and the electric signal is input to the extracting unit 127 (third measuring step).

The extracting unit 127 derives an equation based on the amount PA0 of the excitation light emitted from the excitation light source 103A and the fluorescence intensity PA1 represented by the input electric signal, an equation based on the amount PB0 of the excitation light emitted from the excitation light source 103B and the fluorescence intensity PB1 represented by the input electric signal, and an equation based on the amount PC0 of the excitation light emitted from the excitation light source 103B and the fluorescence intensity PC1 represented by the input electric signal (relational expression step).

Herein, the control unit 131 controls the excitation light source 103A and the excitation light source 103B so that the amount PA0 of the excitation light emitted from the excitation light source 103A and the amount PB0 of the excitation light emitted from the excitation light source 103B are equal to each other. Also, the control unit 131 controls the amount PC0 of the excitation light emitted from the excitation light source 103B so that the intensity PC1 of the fluorescence generated from the subject body 7 is equal to the fluorescence intensity PA1 generated from the subject body 7.

FIG. 12 a schematic view of the subject body 7 to be examined, the view for explaining parameters of the equations derived in the extracting unit 127.

More specifically, the extracting unit 127 derives the following equations (3), (4) and (5):

$$P_{A1} = \int_a^b P_{A0} e^{-\mu_{A0} z} \times C \times e^{-\mu_{A1} z} dz \quad (3)$$

$$= -\frac{P_{A0} C}{\mu_{A0} + \mu_{A1}} [e^{-(\mu_{A0}+\mu_{A1})z}]_a^b$$

$$= \frac{P_{A0} C}{\mu_{A0} + \mu_{A1}} \{e^{-(\mu_{A0}+\mu_{A1})a} - e^{-(\mu_{A0}+\mu_{A1})b}\}$$

$$P_{B1} = \int_a^b P_{B0} e^{-\mu_{B0} z} \times C \times e^{-\mu_{B1} z} dz \quad (4)$$

$$= -\frac{P_{B0} C}{\mu_{B0} + \mu_{B1}} [e^{-(\mu_{B0}+\mu_{B1})z}]_a^b$$

$$= \frac{P_{B0} C}{\mu_{B0} + \mu_{B1}} \{e^{-(\mu_{B0}+\mu_{B1})a} - e^{-(\mu_{B0}+\mu_{B1})b}\}$$

$$P_{C1} = \int_a^b P_{C0} e^{-\mu_{B0} z} \times C \times e^{-\mu_{B1} z} dz \quad (5)$$

$$= -\frac{P_{C0} C}{\mu_{B0} + \mu_{B1}} [e^{-(\mu_{B0}+\mu_{B1})z}]_a^b$$

$$= \frac{P_{C0} C}{\mu_{B0} + \mu_{B1}} \{e^{-(\mu_{B0}+\mu_{B1})a} - e^{-(\mu_{B0}+\mu_{B1})b}\}$$

In those equations, as shown in FIG. 12, a represents a depth from the surface of the subject body 7 to the top of the lesion part T, and b represents a depth from the surface of the subject body 7 to the bottom of the lesion part T. Also, $\mu_{A0}$ is an attenuation coefficient representing a rate at which the excitation light emitted from the excitation light source 103A is absorbed by the subject body 7 until reaching the lesion part T, and $\mu_{A1}$ is an attenuation coefficient representing a rate at which the fluorescence generated from the lesion part T with irradiation of the excitation light emitted from the excitation light source 103A is absorbed until outgoing from the surface of the subject body 7. Further, $\mu_{B0}$ is an attenuation coefficient representing a rate at which the excitation light emitted from the excitation light source 103B is absorbed by the subject body 7 until reaching the lesion part T, and $\mu_{B1}$ is an attenuation coefficient representing a rate at which the fluorescence generated from the lesion part T with irradiation of the excitation light emitted from the excitation light source 103B is absorbed until outgoing from the surface of the subject body 7. C represents the intensity of the fluorescence generated from the lesion part T per unit volume (i.e., fluorescence concentration).

After the equations have been derived in the extracting unit 127, as shown in FIG. 11, the size (thickness) of the lesion part T is calculated in the extracting unit 127 by setting up simultaneous equations (step S12). More specifically, the extracting unit 127 sets up simultaneous equations, i.e., an equation derived from the equations (3) and (4) under the above-described condition of PA0=PB0 and an equation derived from the equations (3) and (5) under the above-described condition of PA1=PC1, and then solves the simultaneous equations for the depths a and b (calculating step). The difference between the thus-calculated depths a and b represents the thickness of the lesion part T.

After the thickness of the lesion part T has been calculated, as shown in FIG. 11, the extracting unit 127 determines the feature of the lesion part T based on the thickness of the lesion part T (step S13). Generally, the thickness of the lesion part T differs depending on whether the lesion part T is the benign tumor BT or the malignant tumor MT. In other words, the lesion part T having a larger thickness indicates the malignant tumor MT, and the lesion part T having a smaller thickness indicates the benign tumor BT. Accordingly, the extracting unit 127 determines the lesion part T to be the malignant tumor MT when the calculated thickness of the lesion part T is larger than a predetermined value, and to be the benign tumor BT when the calculated thickness of the lesion part T is smaller than the predetermined value (determining step).

After the determination, as shown in FIG. 11, the subject body 7 is displayed in a color-coded manner (step S14). More specifically, as shown in FIG. 10, the extracting unit 127 outputs the result of the determination for the lesion part T to the image producing unit 29. Based on the determination result, the image producing unit 29 produces image data of the subject body 7 which represents the lesion part T in a color-coded manner. The color-coded display is performed such that the normal part N, the benign tumor BT, and the malignant tumor MT are visually discriminated from one another. The image data produced by the image producing unit 29 is output to the monitor 15 and is displayed on the monitor 15.

With the arrangement described above, since the endoscope device includes the light source 103 for emitting the excitation lights, the control unit 131 for controlling the wavelengths and the amounts of the excitation lights, the fluorescence detector 11 for measuring the intensities of the fluorescences generated with irradiation of the excitation lights, and the extracting unit 127 for extracting the lesion part T based on the amounts of the excitation lights and the fluorescence intensity, the lesion part T in the subject body 7 can be easily determined.

The light source 103 can change the wavelengths and the amounts of the excitation lights under control of the control unit 131. The fluorescence detector 11 can measure the respective intensities of the fluorescences generated with irradiation of the excitation lights differing in wavelength and amount. Based on the amounts of the excitation lights and the fluorescence intensities, the extracting unit 127 can extract the lesion part T from the normal part N of the subject body 7.

When the excitation light is irradiated in the same amount, the intensity of the fluorescence generated from the lesion part T is larger than that generated from the normal part N. Therefore, the extracting unit 127 can extract a portion of the subject body 7, which is possibly the lesion part T, based on the difference between the intensity of the fluorescence generated from the normal part N and the intensity of the fluorescence generated from the lesion part T.

The intensity of the fluorescence measured by the fluorescence detector 11 depends on the thickness of the lesion part T generating the fluorescence, the depth from surface of the subject body 7 to the position where the lesion part T is present in the subject body 7, the attenuation rate of the excitation light in the subject body 7, and the attenuation rate of the fluorescence in the subject body 7. The extracting unit 127 can determine a plurality of relationships between the amounts of the excitation lights and the fluorescence intensities for the lesion part T, thereby calculating the thickness of the lesion part T based on the plurality of relationships thus determined.

In general, for a portion of the subject body 7 which is possibly the lesion part T, the thickness of such a portion can be used as a parameter for determining whether the relevant portion is the normal part N or the lesion part T. Stated another way, when the thickness of the relevant portion is larger than a predetermined value, it can be determined to be the lesion part T, and when the thickness of the relevant portion is smaller than the predetermined value, it can be determined to be the normal part N. Accordingly, the extracting unit 127 can extract the lesion part T based on the thickness of the portion of the subject body 7, which is possibly the lesion part T. Further, based on the thickness of the lesion part T, the extracting unit 127 can determine whether the lesion part T is the benign tumor BT or the malignant tumor MT.

Since the endoscope device includes the image producing unit 29 for producing an image based on the output of the extracting unit 127 and the monitor 15 for displaying the produced image, the lesion part T can be confirmed on the displayed image and the determination of the lesion part T in the subject body 7 can be easily performed.

Since the image producing unit 29 produces an image based on the output of the extracting unit 127, the unit 29 can produce an image that ensures easy confirmation of the lesion part T. Since the monitor 15 displays the image produced by the image producing unit 29, it is possible for, e.g., an operator of the endoscope device 101 to easily recognize, e.g., the shape of the lesion part T and to easily determine the lesion part T.

The observation method using the endoscope device 101 of the second embodiment can easily discriminate the lesion part T by including step S11 of deriving equations representing the relationships between the intensities of the fluorescences generated from the lesion part T, etc. and the amounts of the excitation lights, step S12 of calculating the thickness of the lesion part T, etc., and step S13 of determining a characteristic of the lesion part T, etc.

In step S11, the intensities of the fluorescences generated from the lesion part T, etc. with irradiation of the excitation lights having different wavelengths and different amounts are measured and the equations are derived based on the amounts of the excitation lights and the fluorescence intensities thus measured. In step S12, the thickness of the lesion part T, etc. can be calculated by setting up a plurality of equations and solving the simultaneous equations. In step S13, the lesion part T, etc. can be determined based on the calculated thickness of the lesion part T, etc. In addition, it is also possible to determine whether the lesion part T is the benign tumor BT or the malignant tumor MT.

Since step S11 is executed to measure the fluorescence intensities with respect to the excitation lights differing in wavelength and amount and to derive the plurality of equations representing the relationships between the amounts of the excitation lights and the fluorescence intensities, the plurality of equations can be easily derived.

In the equation based on the amount PA0 of the excitation light and the fluorescence intensity PA1 (i.e., the equation (3)) and in the equation based on the amount PB0 of the excitation light and the fluorescence intensity PB1 (i.e., the equation (4)), the amounts of the excitation lights are the same. Also, in the equation based on the amount PA0 of the excitation light and the fluorescence intensity PA1 (i.e., the equation (3)) and in the equation based on the amount PC0 of the excitation light and the fluorescence intensity PC1 (i.e., the equation (5)), the fluorescence intensities are the same. Therefore, the thickness of the lesion part T can be calculated by setting up an equation derived from the equations (3) and (4) and an equation derived from the equations (3) and (5), and solving the simultaneous equations.

What is claimed is:

1. A lesion extracting device comprising:
    excitation light emitting means for emitting an excitation light toward a subject body to be examined;
    control means for changing an amount of the excitation light;
    light irradiating and receiving means for irradiating the excitation light to the subject body and receiving fluorescence generated from the subject body;
    distance holding means for holding a distance between the subject body and the light irradiating and receiving means at a predetermined value;
    measuring means for measuring a change in the intensity of the fluorescence with respect to a change in the amount of the excitation light, the intensity of fluorescence being received by the light irradiating and receiving means; and
    extracting means for calculating a ratio of the change in the intensity of fluorescence on the basis of a ratio of the change in the amount of the excitation light to the change in the intensity of fluorescence and for extracting a lesion part of the subject body on the basis of the ratio of the changes in the amount of the excitation light to the ratio of the changes in the intensity of fluorescence.

2. A lesion extracting device comprising:
    excitation light emitting means for emitting excitation light at variable wavelengths and variable amounts toward a lesion part of a subject body;
    control means for controlling the excitation light emitting means to emit:
        a first excitation light of a first wavelength and a first amount,
        a second excitation light of a second wavelength and a second amount, and a third excitation light of a third wavelength and a third amount;

measuring means for measuring:
- a first intensity of fluorescence emitted by the subject body when the subject body is irradiated by the first excitation light,
- a second intensity of fluorescence emitted by the subject body when the subject body is irradiated by the second excitation light, and
- a third intensity of fluorescence emitted by the subject body when the subject body is irradiated by the third excitation light;

the control means further controls the excitation light emitting means to emit:
- the first excitation light and the second excitation light such that the first amount is equal to the second amount, and
- the third excitation light such that the first intensity of fluorescence is equal to the third intensity of fluorescence; and extracting means:
for deriving:
- a first equation based on the first amount of the first excitation light and the first intensity of fluorescence,
- a second equation based on the second amount of the second excitation light and the second intensity of fluorescence, and
- a third equation based on the third amount of the third excitation light and the third intensity of fluorescence, for deriving:
- a fourth equation based on the first equation and the second equation, under the condition that the first amount is equal to the second amount, and
- a fifth equation based on the first equation and the third equation, under the condition that the first intensity of fluorescence is equal to the third intensity of fluorescence, for solving the fourth equation and the fifth equation to calculate:
- a first depth from a surface of the subject body to a top of the lesion part of the subject body, and
- a second depth from a surface of the subject body to a bottom of the lesion part, for calculating a difference between the first depth and the second depth as the thickness of the lesion part, and for determining a feature of the lesion part based on the thickness of the lesion part.

3. A lesion extracting device comprising:

excitation light emitting means for emitting an excitation light toward a subject body to be examined;

control means for changing an amount of the excitation light;

light irradiating and receiving means for irradiating the excitation light to the subject body and receiving fluorescence generated from the subject body;

distance holding means for holding a distance between the subject body and the light irradiating and receiving means at a predetermined value;

measuring means for measuring a change in the intensity of the fluorescence with respect to a change in the amount of the excitation light, the intensity of fluorescence being received by the light irradiating and receiving means; and extracting means for calculating a ratio of the changes in the intensity of fluorescence and the changes in the amount of the excitation light, and for extracting a lesion part of the subject body on the basis of the calculated ratio of the changes in the intensity of fluorescence and the changes in the amount of the excitation light.

* * * * *